United States Patent [19]

Hommeltoft

[11] Patent Number: 5,675,053
[45] Date of Patent: Oct. 7, 1997

[54] ALKYLATION PROCESS

[75] Inventor: Sven Ivar Hommeltoft, Hillerød, Denmark

[73] Assignee: Haldor Topsoe A/S, Denmark

[21] Appl. No.: 566,186

[22] Filed: Dec. 1, 1995

[30] Foreign Application Priority Data

Dec. 2, 1994 [DK] Denmark .................................. 1380/94

[51] Int. Cl.$^6$ .................................................. C07C 2/62
[52] U.S. Cl. .................................................. 585/730; 585/720
[58] Field of Search .................................... 585/720, 730

[56] References Cited

U.S. PATENT DOCUMENTS

| | | | |
|---|---|---|---|
| 4,044,069 | 8/1977 | Bernard et al. | 585/730 |
| 4,056,578 | 11/1977 | McClure et al. | 585/730 |
| 5,202,518 | 4/1993 | Del Rossi | 585/730 |
| 5,220,095 | 6/1993 | Hommeltoft et al. | 585/720 |
| 5,245,100 | 9/1993 | Hommeltoft et al. | 585/720 |
| 5,475,184 | 12/1995 | Joly et al. | 585/730 |
| 5,498,820 | 3/1996 | Hommeltoft | 585/730 |

*Primary Examiner*—Ellen M. McAvoy
*Attorney, Agent, or Firm*—Ostrolenk, Faber, Gerb & Soffen, LLP

[57] ABSTRACT

Improved process for the supported liquid phase alkylation of an aliphatic hydrocarbon feedstock in the presence of a fluorinated sulphonic acid catalyst with an olefinic alkylating agent in a reactor containing a fixed bed of particular polar contact material, wherein a reaction zone with the fluorinated sulphonic acid catalyst is moveable established by absorbing the acid catalyst within a confined area of the contact material and passing a process stream of the aliphatic hydrocarbon feedstock and the olefinic alkylating agent through the reactor and the reaction zone, and withdrawing an alkylated product stream from the reactor, wherein the improvement comprises introduction of the fluorinated sulphonic acid alkylation catalyst into the reactor dissolved in a hydrocarbon solvent comprises $C_3$–$C_9$ hydrocarbons and adsorption of the acid catalyst in the solution of the hydrocarbon solvent on the contact material at inlet end of the reactor.

11 Claims, 1 Drawing Sheet

ALKYLATION PROCESS

BACKGROUND OF THE INVENTION

1. Field of the Invention

The present invention relates to improvements in the supported liquid phase alkylation of aliphatic hydrocarbons in the presence of a fluorinated sulphonic acid catalyst.

2. Description of the Related Art

Acid catalyzed alkylation of aliphatic hydrocarbons with olefinic hydrocarbons is a well known process for the preparation of high octane gasoline products. In the past, alkylation of hydrocarbons has been accomplished in liquid phase by mixing paraffins and olefins in the presence of a strong acid catalyst and stirring the mixture until the alkylation reaction was completed.

Presently, the acid catalysts usually employed in the industrial alkylation of aliphatic hydrocarbons are concentrated sulfuric acid or anhydrous hydrofluoric acid, which strength may be increased by addition of a Lewis acid, such as $BF_3$ or $SbF_5$.

Further alkylation catalysts are fluorinated sulfonic acids, as disclosed in U.S. Pat. Nos. 5,220,095 and 5,245,100.

In the process of U.S. Pat. Nos. 5,220,095 and 5,245,100 utilizing fluorinated sulfonic acid alkylation catalysts, a reaction zone is established on solid contact material having the fluorinated sulfonic acid catalyst adsorbed within a confined area of the contact material. In the reaction zone, the process stream is converted under alkylating conditions to a product stream of alkylated hydrocarbons by catalysis of the fluorinated sulfonic acid adsorbed on the contact material.

During the alkylation reaction, the reaction zone moves continuously from the inlet towards the outlet end of the alkylation reactor by interaction with the process stream flowing through and reacting in the zone.

In the process of U.S. Pat. No. 5,245,100, the acid catalyst being adsorbed on the contact material passes by interaction with the process stream sequentially through a first and second reactor. The catalyst is recycled to the first reactor after having passed through the second reactor.

In an industrial alkylation reactor being operated under the above conditions, the cross sectional diameter of the reaction zone will typically be larger than the length of the reaction zone. It is, therefore, necessary to introduce the acid catalyst consistently on the top of the contact material, during transference of the catalyst between the reactor, in order to prevent maldistribution when the reaction zone passes through the reactor as mentioned above.

Maldistribution on top of the reactor will result in distortion of the reaction zone during passage of the process stream through the reactor and movement of the reaction zone.

SUMMARY OF THE INVENTION

It has now been observed that distribution of the catalyst on top of an alkylation reaction can be improved, when introducing the catalyst dissolved homogeneously in a solvent.

It has further been observed that fluorinated sulfonic acid catalysts are soluble in a solvent of $C_3$–$C_9$ hydrocarbons.

Based on the above observations, the invention provides an improvement process for supported liquid phase alkylation of an aliphatic hydrocarbon feedstock in the presence of a fluorinated sulfonic acid catalyst with an olefinic alkylating agent in a reactor containing a fixed bed of a particulate polar contact material, wherein a reaction zone with the fluorinated sulfonic acid catalyst is moveable established by adsorbing the acid catalyst within a confined area of the contact material and passing a process stream of the aliphatic hydrocarbon feedstock and the olefinic alkylating agent through the reactor and the reaction zone, and withdrawing an alkylated product stream from the reactor, wherein the improvement comprises steps of introducing the fluorinated sulfonic acid alkylation catalyst into the reactor dissolved in a hydrocarbon solvent comprising $C_3$–$C_9$ hydrocarbons; and adsorbing the acid catalyst dissolved in the hydrocarbon solvent on the contact material at inlet end of the reactor.

Preferred solvents for obtaining a homogeneous acid catalyst solution comprise $C_3$–$C_5$ hydrocarbons.

The above process is, in particular, useful in an alkylation process being performed in at least two reactors connected in series. Thereby, the acid catalyst leaving a first reactor is introduced on top of a subsequent reactor as previously described in U.S. Pat. No. 5,245,100, which by reference is incorporated herein.

When performing the alkylation process in two or more reactors, it is preferred to arrange a mixing unit between the outlet of the first reactor and the inlet of a subsequent reactor. In the unit, the acid catalyst is mixed and dissolved with the hydrocarbon solvent. The solvent is, preferably, a process stream leaving the first reactor, in order to prevent transfer of a separate acid phase to the inlet of the second reactor.

BRIEF DESCRIPTION OF THE DRAWINGS

The above features and advantages of the invention will further be illustrated in the following Examples by reference to the drawings, in which the sole FIGURE shows a reactor system with two alkylation reactors connected via a mixing unit.

DETAILED DESCRIPTION OF THE PREFERRED EMBODIMENTS

EXAMPLE 1

Figure 1:
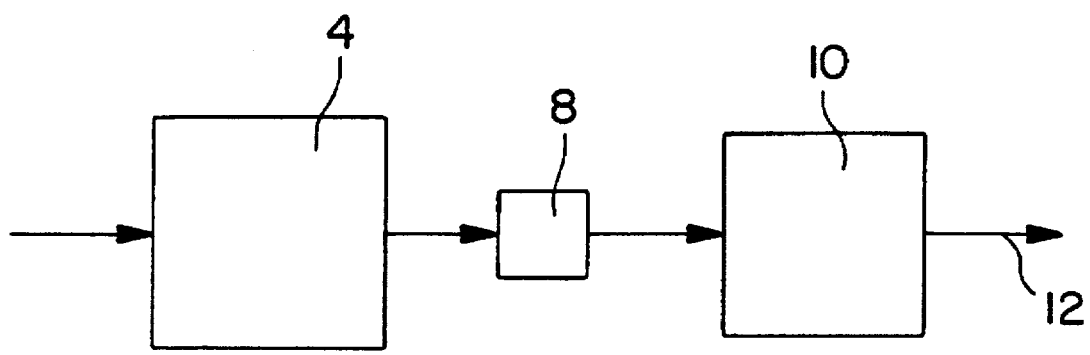

The reaction system used in this and the following Examples is shown in the FIGURE. Alkylation of paraffins with olefins was carried out by passing a feed stream of 5% by weight 2-butene in isobutane at a mass flux of 1000 g/cm$^2$. h and at a temperature of 0°–80° C. through a first alkylation reactor (4) and an effluent stream leaving the first reactor to a mixing unit (8) being connected to the outlet end of the first reactor. Reactor (4) and (10) had a total length of 6 m, each with a diameter (i.d.) of ¼. The volume of mixing unit (8) was 40 ml. The reactors were loaded with each 100 ml of silica (Merck 100) contact material. At the inlet of reactor (4), 6 ml of trifluoromethanesulfonic acid alkylation catalyst were applied on the contact material at the beginning of the process. After passage through the mixing unit (8), the effluent stream was introduced into the second reactor (10), from which a product stream of alkylated product (12) was withdrawn and analyzed.

Comparison Example A

A feed stream as specified in Example 1 was treated by a process similar to that of Example 1, except that the effluent stream leaving the first reactor was directly passed to the second reactor without passage through the mixing unit.

Further process conditions and results obtained by the above Example 1 and Comparison Example A are summarized in the following Table 1 and Table 2, respectively.

EXAMPLE 1

A feed stream of 7.5% by weight propene in isobutane was passed through the reaction system as described in Example 1 at a mass flux of 1000 g/cm$^2$. h and a temperature between 0°–40° C.

Comparison Example B

The feed stream of Example 2 was passed through a reaction system as described above, except that the effluent stream from the first reactor was directly passed to the second reactor without passage through the mixing unit.

The process conditions and results obtained by Example 2 and Comparison Example B are summarized in the following Table 3 and Table 4, respectively.

TABLE 1

| Temp. | 0 | 10 | 20 | 30 | 40 | 60 | 80 |
|---|---|---|---|---|---|---|---|
| C5 | 3.52 | 3.14 | 3.49 | 3.91 | 8.04 | 9.00 | 21.30 |
| C6 | 2.04 | 2.19 | 2.55 | 2.95 | 5.50 | 8.59 | 11.50 |
| C7 | 2.76 | 3.16 | 3.93 | 4.74 | 7.46 | 10.67 | 10.40 |
| C8 | 83.85 | 83.31 | 79.95 | 74.51 | 65.94 | 57.87 | 43.49 |
| C9 | 2.15 | 2.12 | 2.79 | 3.82 | 5.19 | 6.95 | 6.76 |
| C10+ | 5.68 | 6.08 | 7.29 | 10.08 | 7.88 | 6.92 | 6.55 |
| RON (Calc.) | 98 | 97 | 95 | 93 | 90 | 86 | 87 |
| MON (Calc.) | 94 | 94 | 92 | 90 | 88 | 85 | 85 |

TABLE 2

| Temp. | 0 | 10 | 20 | 25 | 30 |
|---|---|---|---|---|---|
| C6 | 1.830 | 1.476 | 3.311 | 4.151 | 4.673 |
| C7 | 2.378 | 2.375 | 4.602 | 5.608 | 6.240 |
| C8 | 90.085 | 89.126 | 82.049 | 79.690 | 77.349 |
| C9 | 1.487 | 1.733 | 2.734 | 3.436 | 3.712 |
| C10+ | 4.221 | 5.291 | 7.304 | 7.115 | 8.025 |
| RON (Calc.) | 98 | 98 | 95 | 94 | 93 |
| MON (Calc.) | 95 | 95 | 93 | 91 | 91 |

TABLE 3

| Temp. | 0 | 10 | 20 | 30 | 40 |
|---|---|---|---|---|---|
| C6 | 4.456 | 3.624 | 10.624 | 5.060 | 6.440 |
| C7 | 25.736 | 30.790 | 37.117 | 37.453 | 38.236 |
| C8 | 47.056 | 43.197 | 36.535 | 40.417 | 39.103 |
| C9 | 10.313 | 10.379 | 8.261 | 9.007 | 8.764 |
| C10+ | 12.384 | 11.959 | 7.411 | 8.019 | 7.398 |
| RON (Cal.) | 90 | 90 | 88 | 88 | 87 |
| MON (Cal.) | 89 | 88 | 86 | 86 | 85 |

TABLE 4

| Temp. | 0 | 10 | 20 | 25 |
|---|---|---|---|---|
| C6 | 7.261 | 8.411 | 8.807 | 9.702 |
| C7 | 27.552 | 32.294 | 35.829 | 37.490 |
| C8 | 40.769 | 40.609 | 38.543 | 38.658 |
| C9 | 10.791 | 9.079 | 7.939 | 7.109 |
| C10+ | 13.611 | 9.578 | 8.843 | 6.993 |
| RON (Calc.) | 90 | 91 | 90 | 89 |

TABLE 4-continued

| Temp. | 0 | 10 | 20 | 25 |
|---|---|---|---|---|
| MON (Calc.) | 88 | 88 | 88 | 87 |

EXAMPLE 3

A feed stream of 20% (w/w) propylene and 80% (w/w) isobutene was reacted by a process and in a reaction system as described in Example 1 above. Prior to introduction into the first reactor, the feed stream was diluted with part of the product stream being withdrawn from the second reactor and recycled from the outlet of the reactor to the inlet of the first reactor. The olefin concentration at inlet of the first reactor was, thereby, adjusted to 2.0% (w/w) at a total hydrocarbon mass flux through the reaction system of 4200 g/cm$^2$h. At the above process conditions, pressure drop in the reactors was between 10 and 12 bar. The composition of the product stream was as follows:

| | |
|---|---|
| $C_5$ | 19.8% (w/w) |
| $C_6$ | 11.3% (w/w) |
| $C_7$ | 24.2% (w/w) |
| $C_8$ | 19.5% (w/w) |
| $C_9$ | 13.5% (w/w) |
| $C_{10}$ | 11.7% (w/w) |
| RON (estimated) 87 | |
| MON (estimated) 87 | |

Comparison Example C

In a process and reaction system as described above in Example 3, isobutane was alkylated with propylene except that the system was not provided with a mixing unit between the reactors. The effluent from the first reactor was directly passed to the second reactor. As a result, the pressure drop in the reactors increased to 27–34 bar. The composition of the product stream obtained in this Example was similar to that of Example 3.

As apparent from the above Examples and results, dissolution of the acid alkylation catalyst prior to introduction into the alkylation reactor results in a much decreased pressure drop.

At the same time, product composition of alkylate product obtained in the inventive process is substantially unchanged when compared to a process without dissolution of the alkylation catalyst prior to introduction into the reaction system.

Although the present invention has been described in relation to particular embodiments thereof, many other variations and modifications and other uses will become apparent to those skilled in the art. Therefore, the present invention is to be limited not by the specific disclosure herein, but only by the appended claims.

I claim:

1. Improved process for the supported liquid phase alkylation of an aliphatic hydrocarbon feedstock in the presence of a fluorinated sulfonic acid catalyst with an olefinic alkylation agent in a reactor containing a fixed bed of particulate polar contact material, wherein a reaction zone with the fluorinated sulfonic acid catalyst is movable established by adsorbing the acid catalyst within a confined area of the contact material and passing a process stream of the aliphatic hydrocarbon feedstock and the olefinic alklyating agent through the reactor and the reaction zone, and withdrawing an alkylated product stream from the reactor, wherein the improvement comprises the steps of:

mixing and dissolving the fluorinated sulfonic acid alkylation catalyst in a hydrocarbon solvent, the solvent comprising $C_3$–$C_9$ hydrocarbons;

introducing the fluorinated sulfonic acid alkylation catalyst into the reactor dissolved in the hydrocarbon solvent; and adsorbing the acid catalyst in the solution of the hydrocarbon solvent on the contact material at an inlet end of the reactor.

2. The process of claim 1, wherein the hydrocarbon solvent comprises $C_3$–$C_5$ hydrocarbons.

3. The process of claim 1, wherein the hydrocarbon solvent is a process stream being withdrawn from the reactor.

4. The process of claim 1, further comprising a first alkylation reactor and a second reactor, wherein the step of dissolving the fluorinated sulfonic acid alkylation catalyst in a hydrocarbon solvent comprises the steps of:

withdrawing the acid catalyst from the first alkylation reactor;

mixing and dissolving the acid catalyst with at least a part of the process stream from the first reactor to produce a dissolved acid catalyst; and introducing the dissolved acid catalyst into the second reactor.

5. The process of claim 2, further comprising a first alkylation reactor and a second reactor, wherein the step of dissolving the fluorinated sulfonic acid alkylation catalyst in a hydrocarbon solvent comprises the steps of:

withdrawing the acid catalyst from the first alkylation reactor;

mixing and dissolving the acid catalyst with at least a part of the process stream from the first reactor to produce a dissolved acid catalyst; and introducing the dissolved acid catalyst into the second reactor.

6. The process of claim 3, further comprising a first alkylation reactor and a second reactor, wherein the step of dissolving the fluorinated sulfonic acid alkylation catalyst in a hydrocarbon solvent comprises the steps of:

withdrawing the acid catalyst from the first alkylation reactor;

mixing and dissolving the acid catalyst with at least a part of the process stream from the first reactor to produce a dissolved acid catalyst; and introducing the dissolved acid catalyst into the second reactor.

7. The process of claim 1, further comprising at least two reactors, wherein the step of mixing and dissolving the fluorinated sulfonic acid alkylation catalyst in a hydrocarbon solvent comprises recycling the alkylation catalyst from one of the reactors to the other.

8. The process of claim 1, further comprising a mixing unit coupled to the reactor, wherein the step of mixing and dissolving the fluorinated sulfonic acid alkylation catalyst in a hydrocarbon solvent comprises the step of mixing the fluorinated sulfonic acid alkylation catalyst and the hydrocarbon solvent together in the mixing unit.

9. The process of claim 4, further comprising a mixing unit coupled to the first and second reactors, wherein the step of mixing and dissolving the fluorinated sulfonic acid alkylation catalyst in a hydrocarbon solvent comprises the step of mixing the fluorinated sulfonic acid alkylation catalyst and the hydrocarbon solvent together in the mixing unit.

10. The process of claim 5, further comprising a mixing unit coupled to the first and second reactors, wherein the step of mixing and dissolving the fluorinated sulfonic acid alkylation catalyst in a hydrocarbon solvent comprises the step of mixing the fluorinated sulfonic acid alkylation catalyst and the hydrocarbon solvent together in the mixing unit.

11. The process of claim 6, further comprising a mixing unit coupled to the first and second reactors, wherein the step of mixing and dissolving the fluorinated sulfonic acid alkylation catalyst in a hydrocarbon solvent comprises the step of mixing the fluorinated sulfonic acid alkylation catalyst and the hydrocarbon solvent together in the mixing unit.

* * * * *